(12) United States Patent
Evans et al.

(10) Patent No.: US 12,426,871 B2
(45) Date of Patent: Sep. 30, 2025

(54) SYSTEMS, DEVICES AND METHODS FOR IMPLANTING SUTURE BUTTONS

(71) Applicant: GLOBUS MEDICAL, INC., Audubon, PA (US)

(72) Inventors: Peter Evans, Lafayette Hill, PA (US); David Laird, Sr., Brandamore, PA (US); Megan Duman, Horsham, PA (US); Peter M. Govey, Ardmore, PA (US); Michelle Gray, Oley, PA (US); Bradford H. Rippe, Media, PA (US); Donald Anding, Philadelphia, PA (US); Blaize Majdic, King of Prussia, PA (US); Anthony Nicaretta, Glenside, PA (US)

(73) Assignee: Globus Medical, Inc., Audubon, PA (US)

( * ) Notice: Subject to any disclaimer, the term of this patent is extended or adjusted under 35 U.S.C. 154(b) by 386 days.

(21) Appl. No.: 17/821,982

(22) Filed: Aug. 24, 2022

(65) Prior Publication Data

US 2024/0065686 A1     Feb. 29, 2024

(51) Int. Cl.
*A61B 17/04* (2006.01)
*A61B 17/80* (2006.01)
*A61B 17/84* (2006.01)

(52) U.S. Cl.
CPC ...... *A61B 17/0401* (2013.01); *A61B 17/8061* (2013.01); *A61B 17/842* (2013.01); *A61B 2017/0404* (2013.01); *A61B 2017/0409* (2013.01); *A61B 2017/0477* (2013.01)

(58) Field of Classification Search
CPC ............ A61B 17/0401; A61B 17/8061; A61B 17/842; A61B 2017/0404; A61B 2017/0409; A61B 2017/0477; A61B 17/16; A61B 2017/0459; A61B 90/03; A61B 2017/0496; A61B 17/0483; A61B 2017/0414; A61B 2017/0417
See application file for complete search history.

(56) References Cited

U.S. PATENT DOCUMENTS 4,959,064 A   9/1990   Englehardt
5,041,129 A   8/1991   Hayhurst et al.
(Continued)

FOREIGN PATENT DOCUMENTS

AU   202200860        3/2022
AU   2022200860 A1    3/2022
(Continued)

*Primary Examiner* — Andrew P. Restaino

(57) ABSTRACT

A suture button system for fixing a syndesmotic injury comprises a flexible fixation implant and an inserter device used to deploy the implant across bones. The flexible fixation implant typically comprises a flexible connector and two suture buttons which interface with the bone surface or a bone plate or washer. The flexible connector comprises a plurality of suture strands. The buttons typically have a feature which allows them to interface with an instrument used to deploy the implant across the two bones. The inserter device is configured to interface with the flexible fixation implant and to position it across bones through a pre-drilled bone tunnel. The inserter device may comprise a cannulated insertion rod and a handle.

14 Claims, 17 Drawing Sheets

(56) References Cited

U.S. PATENT DOCUMENTS

| | | | |
|---|---|---|---|
| 5,674,247 A * | 10/1997 | Sohn | A61B 17/0401 606/232 |
| 6,736,819 B2 | 5/2004 | Tiperneni | |
| 6,761,722 B2 | 7/2004 | Cole et al. | |
| 7,097,654 B1 | 8/2006 | Freedland | |
| 7,235,091 B2 | 6/2007 | Thornes | |
| 7,591,823 B2 | 9/2009 | Tiperneni | |
| 7,594,923 B2 | 9/2009 | Fallin et al. | |
| 7,625,395 B2 | 12/2009 | Muckter | |
| 7,658,751 B2 | 2/2010 | Stone et al. | |
| 7,686,838 B2 | 3/2010 | Wolf et al. | |
| 7,875,057 B2 | 1/2011 | Cook et al. | |
| 7,875,058 B2 | 1/2011 | Holmes, Jr. | |
| 7,901,431 B2 | 3/2011 | Tiperneni | |
| 7,955,388 B2 | 6/2011 | Jensen et al. | |
| 7,959,650 B2 | 6/2011 | Kaiser et al. | |
| 7,963,966 B2 | 6/2011 | Cole | |
| 8,137,382 B2 | 3/2012 | Denham et al. | |
| 8,162,997 B2 | 4/2012 | Struhl | |
| 8,202,298 B2 | 6/2012 | Cook et al. | |
| 8,221,455 B2 | 7/2012 | Shurnas et al. | |
| 8,231,654 B2 | 7/2012 | Kaiser et al. | |
| 8,267,959 B2 | 9/2012 | Fallman | |
| 8,317,828 B2 | 11/2012 | Martinek et al. | |
| 8,348,960 B2 | 1/2013 | Michel et al. | |
| 8,512,376 B2 | 8/2013 | Thornes | |
| 8,562,647 B2 | 10/2013 | Kaiser et al. | |
| 8,591,578 B2 | 11/2013 | Albertorio et al. | |
| 8,597,337 B2 | 12/2013 | Champagne | |
| 8,679,167 B2 | 3/2014 | Tiperneni et al. | |
| 8,702,768 B2 | 4/2014 | Tiperneni | |
| 8,715,348 B2 | 5/2014 | McNamara et al. | |
| 8,828,067 B2 | 9/2014 | Tiperneni et al. | |
| 8,840,645 B2 | 9/2014 | Denham et al. | |
| 8,870,876 B2 | 10/2014 | Lettman et al. | |
| 8,876,900 B2 | 11/2014 | Guederian et al. | |
| 8,888,815 B2 | 11/2014 | Holmes, Jr. | |
| 8,936,621 B2 | 1/2015 | Denham et al. | |
| 9,005,245 B2 | 4/2015 | Thornes et al. | |
| 9,056,003 B2 * | 6/2015 | Demmer | A61B 17/0401 |
| 9,060,809 B2 | 6/2015 | Tiperneni et al. | |
| 9,072,510 B2 | 7/2015 | Thornes et al. | |
| 9,107,701 B2 | 8/2015 | Cole | |
| 9,138,219 B2 | 9/2015 | Horrell et al. | |
| 9,149,267 B2 | 10/2015 | Norton et al. | |
| 9,179,950 B2 * | 11/2015 | Zajac | A61B 17/842 |
| 9,226,743 B2 | 1/2016 | Dreyfuss et al. | |
| 9,277,912 B2 | 3/2016 | Donate et al. | |
| 9,332,979 B2 | 5/2016 | Sullivan et al. | |
| 9,387,011 B2 | 7/2016 | Chudik | |
| 9,463,013 B2 | 10/2016 | Pilgeram et al. | |
| 9,468,433 B2 | 10/2016 | Denham et al. | |
| 9,498,204 B2 | 11/2016 | Denham et al. | |
| 9,642,609 B2 | 5/2017 | Holmes, Jr. | |
| 9,993,241 B2 | 6/2018 | Denham et al. | |
| 10,022,118 B2 | 7/2018 | Norton et al. | |
| 10,251,686 B2 | 4/2019 | Zajac et al. | |
| 10,285,801 B2 | 5/2019 | Roller et al. | |
| 10,363,028 B2 | 7/2019 | Norton | |
| 10,376,260 B2 | 8/2019 | Bojarski et al. | |
| 10,398,430 B2 | 9/2019 | Stone et al. | |
| 10,441,265 B2 | 10/2019 | Pasquali et al. | |
| 10,448,945 B2 | 10/2019 | Bachmaier et al. | |
| 10,517,587 B2 | 12/2019 | Denham et al. | |
| 10,610,212 B2 | 4/2020 | Breslich | |
| 10,646,327 B2 | 5/2020 | Lund | |
| 10,675,015 B2 | 6/2020 | Guo et al. | |
| 10,716,557 B2 | 7/2020 | Denham et al. | |
| 10,722,344 B2 | 7/2020 | Armington et al. | |
| 10,729,430 B2 | 8/2020 | Denham et al. | |
| 10,758,224 B2 | 9/2020 | Medoff | |
| 10,772,619 B2 | 9/2020 | Brunsvold et al. | |
| 10,898,179 B2 | 1/2021 | Dreyfuss et al. | |
| 10,918,375 B2 | 2/2021 | Thornes | |
| 11,039,826 B2 | 6/2021 | Denham et al. | |
| 11,045,233 B2 | 6/2021 | O'Conner et al. | |
| 11,064,993 B2 | 7/2021 | Brunsvold et al. | |
| 11,071,537 B2 | 7/2021 | Orphanos et al. | |
| 11,109,855 B2 | 9/2021 | Shoshtaev et al. | |
| 11,129,654 B2 | 9/2021 | Zajac et al. | |
| 11,219,444 B2 | 1/2022 | Sikora et al. | |
| 11,229,456 B2 | 1/2022 | Awtrey et al. | |
| 11,259,792 B2 | 3/2022 | Denham et al. | |
| 11,259,794 B2 | 3/2022 | Stone et al. | |
| 11,259,912 B2 | 3/2022 | Albertorio et al. | |
| 11,272,920 B2 | 3/2022 | Gustafson | |
| 11,317,907 B2 | 5/2022 | Denham et al. | |
| 11,529,134 B2 | 12/2022 | Taylor et al. | |
| 2002/0198527 A1 | 12/2002 | Muckter | |
| 2007/0073342 A1 | 3/2007 | Stone et al. | |
| 2007/0225719 A1 * | 9/2007 | Stone | A61B 17/0642 606/232 |
| 2010/0076504 A1 | 3/2010 | McNamara et al. | |
| 2013/0012765 A1 * | 1/2013 | Vemuri | A61B 17/0401 600/30 |
| 2013/0053897 A1 * | 2/2013 | Brown | A61B 17/8861 606/232 |
| 2013/0331886 A1 | 12/2013 | Thornes | |
| 2014/0257294 A1 | 9/2014 | Gedet et al. | |
| 2015/0039029 A1 | 2/2015 | Wade | |
| 2015/0209027 A1 | 7/2015 | Collins et al. | |
| 2015/0342651 A1 | 12/2015 | Cole | |
| 2016/0051250 A1 | 2/2016 | Thornes | |
| 2017/0135691 A1 * | 5/2017 | Branthover | A61B 17/0401 |
| 2017/0172562 A1 | 6/2017 | Lombardo | |
| 2017/0281150 A1 | 10/2017 | Stecco et al. | |
| 2018/0064434 A1 | 3/2018 | Jolly et al. | |
| 2018/0085110 A1 | 3/2018 | Earhart et al. | |
| 2018/0249998 A1 * | 9/2018 | Chavan | A61B 17/0487 |
| 2020/0015804 A1 | 1/2020 | Bachmaier et al. | |
| 2020/0093514 A1 | 3/2020 | Perez et al. | |
| 2020/0179020 A1 | 6/2020 | Zajac et al. | |
| 2020/0367878 A1 | 11/2020 | Thornes | |
| 2021/0068806 A1 * | 3/2021 | Niver | A61B 17/0401 |
| 2021/0128138 A1 | 5/2021 | Bettenga | |
| 2021/0177395 A1 | 6/2021 | Taylor et al. | |
| 2021/0186488 A1 | 6/2021 | Grunden | |
| 2021/0298740 A1 | 9/2021 | Taylor et al. | |
| 2021/0378654 A1 | 12/2021 | Lombardo | |
| 2021/0401567 A1 | 12/2021 | Bachmaier et al. | |
| 2022/0142635 A1 | 5/2022 | Bachmaier et al. | |
| 2022/0233302 A1 | 7/2022 | Malone et al. | |

FOREIGN PATENT DOCUMENTS

| | | |
|---|---|---|
| CN | 106264634 | 7/2019 |
| CN | 112790894 A | 5/2021 |
| CN | 113057699 A | 7/2021 |
| CN | 112790894 | 12/2021 |
| CN | 113057699 | 9/2022 |
| EP | 1791475 | 6/2007 |
| EP | 1331886 B1 | 12/2008 |
| EP | 3527144 A1 | 8/2019 |
| EP | 3917411 | 12/2021 |
| JP | 06114067 | 4/1994 |
| JP | 2006-503655 A | 2/2006 |
| WO | 02/36020 A1 | 5/2002 |
| WO | 2020/180963 A1 | 9/2020 |
| WO | 2021/101724 A1 | 5/2021 |
| WO | 2021/202123 A1 | 10/2021 |
| WO | 2022/055983 A1 | 3/2022 |
| WO | 2022/188376 A1 | 9/2022 |

* cited by examiner

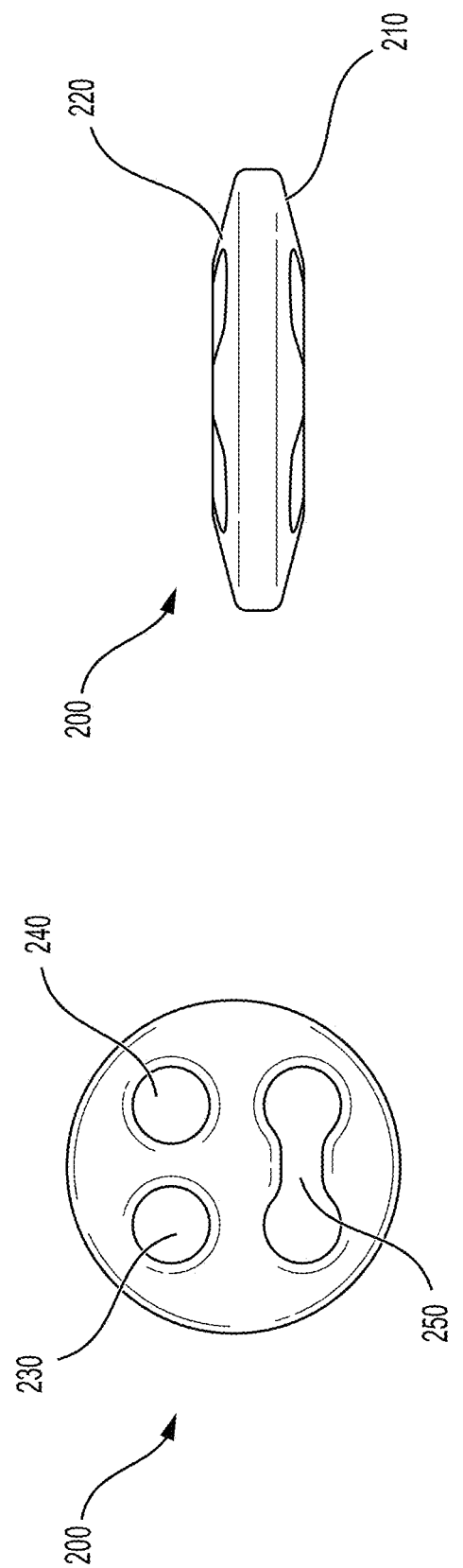

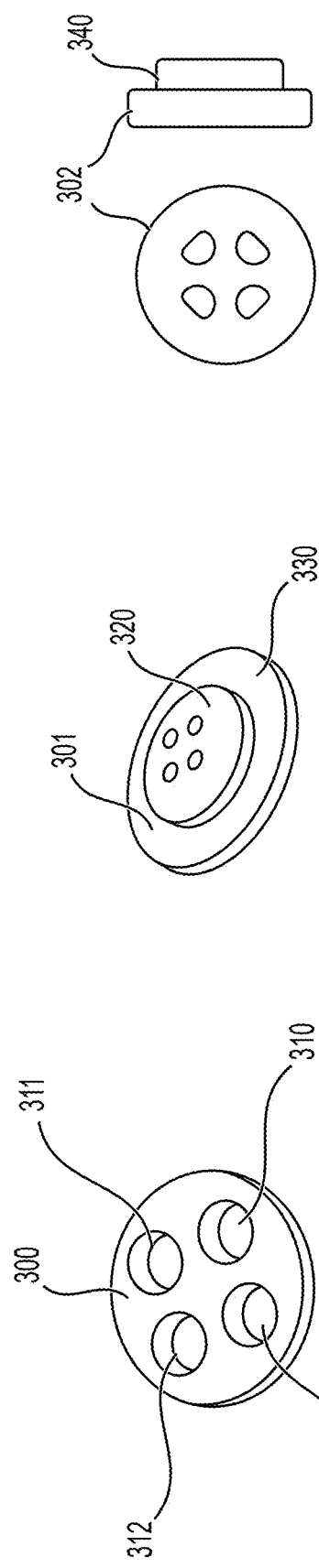
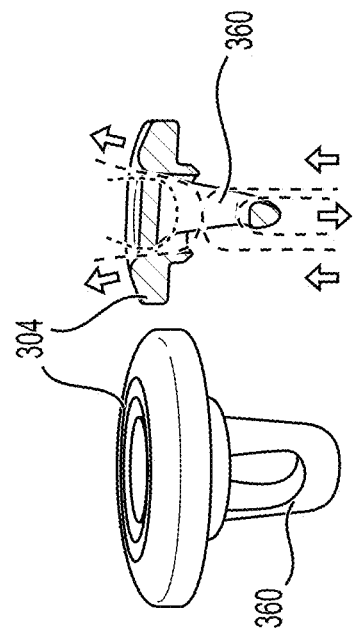
FIG. 3A
FIG. 3B
FIG. 3C
FIG. 3D
FIG. 3E

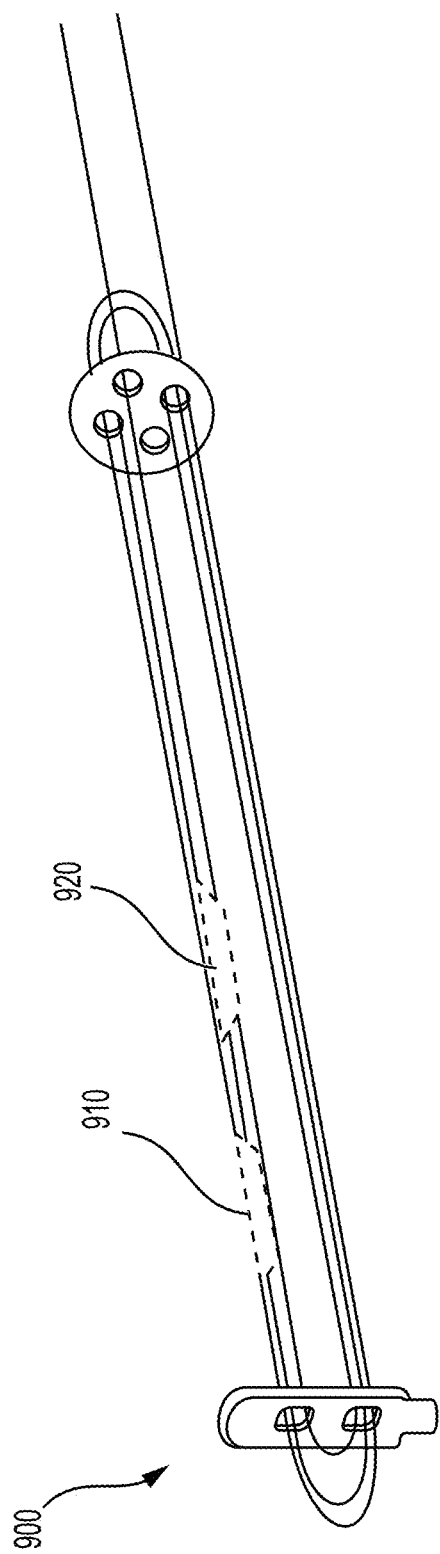

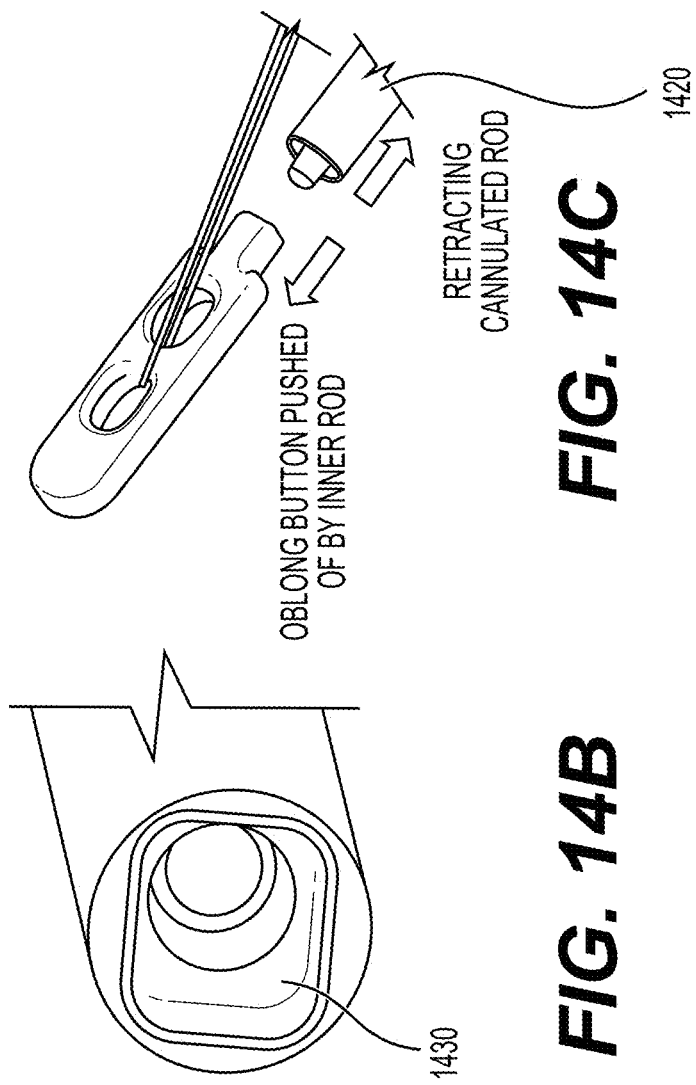
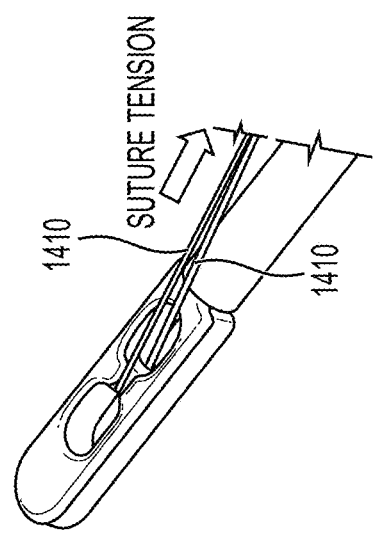
FIG. 14A   FIG. 14B   FIG. 14C

SYSTEMS, DEVICES AND METHODS FOR IMPLANTING SUTURE BUTTONS

FIELD

The present disclosure relates to the field of surgery and in particular to systems, devices, and methods for the stabilization and fixation of bone fractures.

BACKGROUND

The ankle joint is made up of three bones—the tibia and fibula of the lower leg with the talus of the foot. The tibia is a medial or inside anklebone; and the fibula runs parallels to tibia and constitutes the lateral or outside anklebone. One common ankle injury is a disruption of the syndesmosis. A ankle syndesmotic injury is a disruption of the strong fibrous ligaments that hold the fibula and tibia together near the ankle joint. If the syndesmosis is disrupted, then the ankle joint will be unstable and surgery is usually indicated.

The fixation methodologies for ankle syndesmosis rupture have been advanced by the use of flexible suture-button devices to stabilize the distal tibiofibular joint. However, there remains several drawbacks with the current procedures used to achieve that fixation. With current technology, incisions must be made on both sides of the ankle and holes must be drilled entirely through both the fibula and the tibia. In addition, the suture must be manually held under tension while it is manually tied off to complete the fixation. This process often results in undesirable loose suture, which reduces the degree of fixation that can be achieved. Furthermore, multiple knots may be required to tie off the suture, and those knots often can cause soft tissue damages.

Therefore, it is desirable to obtain systems, devices and methods to use in the fixation for ankle syndesmosis injuries that are robust and strong, and that still minimize or eliminate the number and size of the knots to be tied by a surgeon. It is also desirable to provide systems, devices and methods that minimize the number of components that a system needs to attach an suture button to the bone and bring the tissue closer to that bone. There is also a need for suture buttons and methods of positioning such buttons that minimize the surgical trauma associated with the implantation of a button of a certain size.

SUMMARY

The current disclosure provides a suture button system comprising an implantable, flexible fixation construct interfaces with an implant delivery instrument intended to improve ease of insertion and positioning of the construct. In particular, the suture button system is designed to provide flexible fixation for an ankle after disruption of the syndesmosis to enable healing of injured ligaments and soft tissues. The main objectives of the suture button system are to (1) aid in anatomic reduction to improve clinical outcomes, (2) reduce soft tissue damage associated with open surgery, and (3) simplify the intraoperative procedure.

In one embodiment of the disclosure, a suture button system comprises a flexible fixation implant and an inserter device used to deploy the implant across bones. The flexible fixation implant according to the present disclosure typically comprises a flexible connector and two suture buttons or anchors which interface with the bone surface or a bone plate or washer. The flexible connector comprises a plurality of suture strands of braided suture, wire, spring, or other elastic material. The buttons or anchors typically have a feature which allows them to interface with an instrument used to deploy the implant across the two bones. The inserter device is configured to interface with the implant and to position it across bones through a pre-drilled bone tunnel. The inserter device may comprise an cannulated insertion rod and a handle.

In a further non-limiting embodiment of the foregoing system, the flexible fixation implant comprise a medial button and a lateral button, which are meant to be positioned on the medial side of the tibia and the lateral side of the fibula. In various embodiments, the medial button is generally oblong in shape configured to pass through the drilled hole and be deployed on the medial side of the tibia, and the lateral button is circular in shape configured to sit on the lateral side of the fibula, or interface with a fibular plate or washer.

In a further non-limiting embodiment of any of the foregoing system, the flexible connector comprises a plurality of suture strands looped through the medial button and the lateral button. In another embodiment, the suture strand is passed through at least one hole in both the medial button and the lateral button. In another embodiment, the flexible connector comprises at least one free end extending through the lateral button.

In a further non-limiting embodiment of the foregoing system, the flexible connector comprises two self-intersecting loop assemblies, one is positioned through the medial button and the other is positioned between the medial button and the lateral button. The self-intersecting loop assembly is formed by passing one section of the suture strand through another section of the suture strand so that the self-intersecting loop assembly constricts against the section of the suture strand that is passed through when a free end of the suture strand is tightened.

In a further non-limiting embodiment of the foregoing system, one free end of the suture strand is secured to the medial button by means of a hard-stop, tying a knot, attaching the free end to the medial button, or by other means of fixation that prevent pull-through and the opposite end of the suture strand is looped through the lateral button and back through the medial button.

In a further non-limiting embodiment of the foregoing system, the flexible suture connector comprises a suture passage formed by loosening braiding in a portion of a suture strand and splicing another portion of the suture strand through the loosened portion of the suture strand.

In accordance with one embodiment, the present disclosure provides a method for positioning a flexible fixation implant across bones comprising drilling a bone tunnel through from the lateral side of the fibula to the medial side of the tibia; providing an flexible fixation implant comprising a medial button, a lateral button and a flexible connector extending between the buttons; providing an inserter device with a cannulated insertion rod extending from a handle of the inserter device; attaching the medial button to the insertion rod of the inserter device; inserting the medial button through the bone tunnel until the medial button exits on a medial side of the tibia; detaching the medial button from the cannulated insertion rod of the inserter device; positioning the medial button to lie flat against the medial side of the tibia; withdrawing the insertor rod of the inserter device from the bone tunnel; and placing the lateral button to the lateral side of the fibula by applying tension to the flexible connector.

In a further non-limiting embodiment of the foregoing method, attaching the medial button to the insertion rod of the inserter device includes inserting a tab of the medial button into the cannulated insertion rod of the inserter device and pulling the suture strands toward the handle of the inserter device.

In a further non-limiting embodiment of the foregoing method, detaching the medial button from the cannulated insertion rod of the inserter device includes retracting the cannulated rod away from the medial button by means situated on the handle.

In a further non-limiting embodiment of the foregoing method, the flexible connector comprises a plurality of suture strands looped through the medial button and the lateral button. In another embodiment, the suture strand is passed through at least one aperture in both the medial button and the lateral button. In another embodiment, the flexible connector comprises at least one free end extending through the lateral button.

In a further non-limiting embodiment of the foregoing method, positioning the medial button includes applying tension to at least one free end of suture strand until the medial button device pivots from one position generally parallel to the tunnel to another position generally transverse to the tunnel.

In accordance with one embodiment, the present disclosure provides an inserter device for positioning the flexible fixation implant. An exemplary inserter device of the present disclosure comprises a cannulated insertion rod fixedly attached to a handle that houses a structure for disengaging the medial button at the distal tip of the cannulated rod.

In a further non-limiting embodiment of the foregoing device, the medial oblong button is secured to a cannulated rod via inserting a tab situated at one end of the medial button to the distal tip of the cannulated rod. The tab of the medial button along with the tension in the suture lines looped between the medial button and the lateral button positioned on the handle secures the medial button at the distal tip of the cannulated rod.

In a further non-limiting embodiment of the foregoing device, an inserter device may include a handle with a safety tap for preventing accidental button deployment. The safety tap may sit on top of a pullback trigger situated on the handle. Once the safety tap is removed, the pullback trigger can be manipulated to retract the cannulated rod away from the medial button.

In a further non-limiting embodiment of the foregoing device, the inserter device of the present disclosure may include a tensioning handle configured to tension the lateral button. The tensioning handle comprises a detachable proximal portion with two anchor points and a distal housing for housing the lateral button. Each anchor point is located at the opposite lateral side of the proximal portion of the handle. A surgeon may deploy the tensioning handle by turning the proximal portion of the handle a counterclockwise quarter turn and then lifting the proximal portion out of the distal housing. The proximal portion of the handle can then be separated into two halves and held in each hand to provide tensioning of the lateral button.

In a further non-limiting embodiment of the foregoing device, the inserter device of the present disclosure may include a tensioning handle. The tensioning handle comprises a detachable proximal portion and a fixed distal portion. The detachable proximal portion is coupled with the fixed distal portion with mating grooves and a friction fit and the detachable proximal portion may be separated from the fixed distal portion by turning the proximal and distal portions of the handle in opposite directions. In one embodiment, separating the detachable proximal portion from the fixed distal portion may cause to retract the internal rod.

In view of the foregoing, other aspects, features, details, utilities, and advantages of the disclosed embodiments will be apparent from the following description and claims as well as the accompanying drawings.

BRIEF DESCRIPTION OF THE DRAWINGS

The following detailed description and examples are provided for the purpose of non-exhaustively describing some, but not necessarily all, examples or embodiments of the disclosure, and shall not limit the scope of the disclosure in any way.

FIGS. 2A and 2B illustrate a schematic perspective view (FIG. 2A) and a side view (FIG. 2B) of a round lateral button in accordance with the present disclosure.

FIGS. 3A-3H illustrate alternative designs for the round lateral button in accordance with the present disclosure.

FIG. 8 depicts one embodiment of a single splice suture braid assembly in accordance with the present disclosure.

FIG. 9 depicts one embodiment of a single sided double splice braid assembly in accordance with the present disclosure.

FIGS. 14A, 14B, and 14C illustrate tension in the suture lines that prevent the oblong button from popping off the inner insertion rod.

DETAILED DESCRIPTION OF THE EMBODIMENTS

It should be understood that this disclosure is not limited to the particular apparatus, methodology, protocols, and systems, etc., described herein and as such may vary. The terminology used herein is for the purpose of describing particular embodiments only and is not intended to limit the scope of the present disclosure, which is defined solely by the claims.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The following detailed description and the accompanying drawings to which it refers are intended to describe some, but not necessarily all, examples or embodiments of the disclosure. The described embodiments are to be considered in all respects only as illustrative and not restrictive. The contents of this detailed description and the accompanying drawings do not limit the scope of the disclosure in any way.

The present disclosure is directed to systems, devices and methods for deploying a flexible fixation implant across two bones. To illustrate, several exemplary embodiments are described in detail herein. The systems, devices and methods described can be utilized in other contexts.

In one embodiment of the disclosure, a suture button system comprises a flexible fixation implant and an inserter device used to deploy the implant across the two bones. The flexible fixation implant according to the present disclosure typically comprises a flexible connector and two suture buttons or anchors, which interface with the bone surface or a bone plate or washer.

Figure 1:
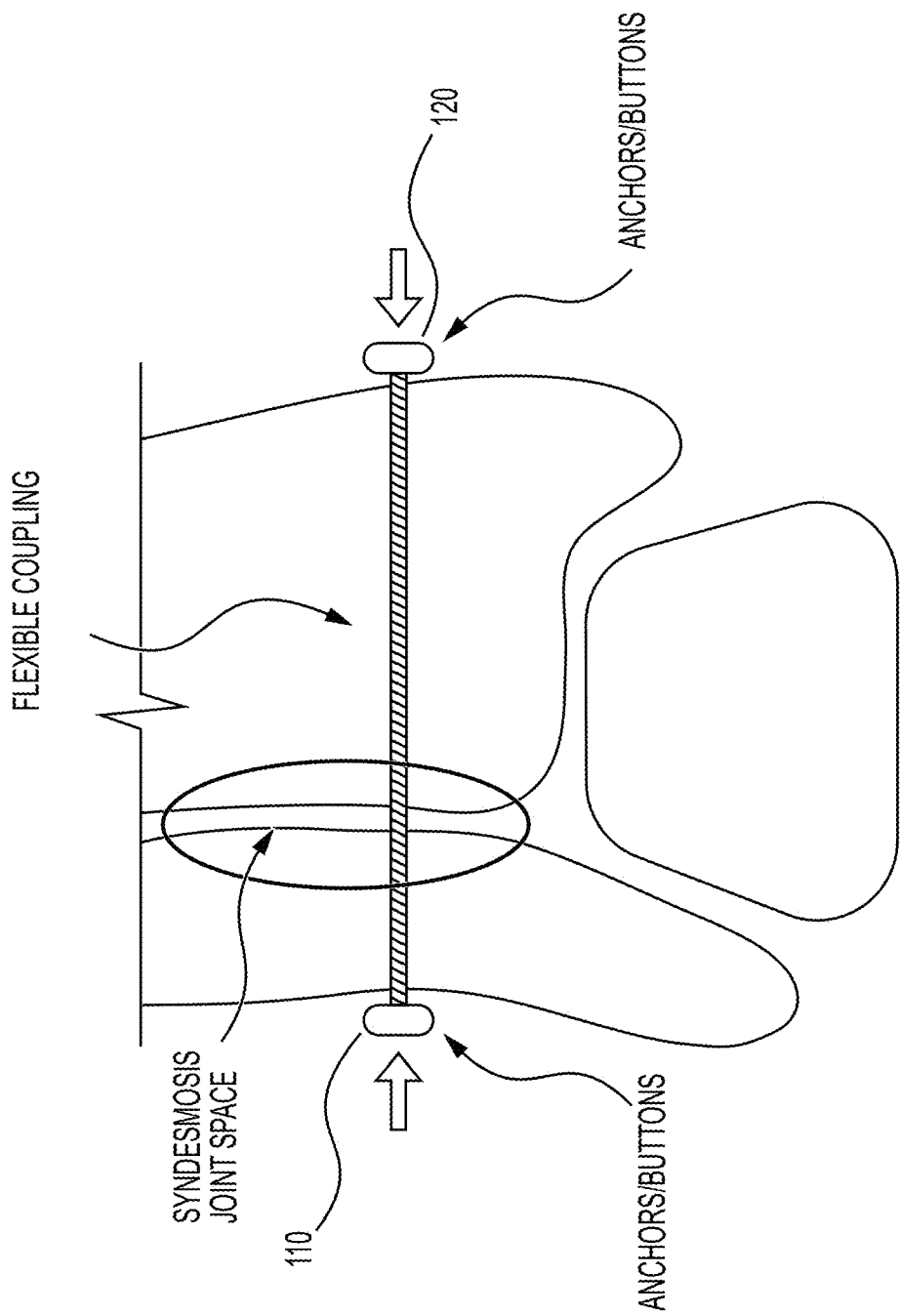
FIG. 1 illustrates a schematic view of a suture button implant positioned across the fibula and tibia bones at the inferior tibiofibular joint.

FIG. 1 illustrates a schematic view of a suture button implant positioned across the fibula and tibia bones at the inferior tibiofibular joint. As illustrated in FIG. 1, the buttons 110, 120 of the flexible implant are meant to sit on the medial side of the tibia and lateral side of the fibula. As a result, the medial 110 and lateral 120 buttons often have different geometries, as the medial button needs to be able to pass through the drilled hole and be deployed on the medial side of the tibia, while the lateral button needs to be able to sit on the lateral side of the fibula independently, or interface with a fibular plate or washer. In various embodiments, the medial button generally has an oblong configuration with two apertures and rounded edges, and the lateral button has a circular configuration.

FIGS. 2A and 2B illustrate a schematic perspective view (FIG. 2A) and a side view (FIG. 2B) of a round lateral button in accordance with the present disclosure. A lateral button 200 has a standard circular shape to allow compatibility with ankle plating and two-hole washers, and incorporates a beveled outer edge 210 for less soft tissue irritation. This is especially important for the lateral side of the fibula where this button is placed as the bone surface is very close to the skin with a very limited amount of soft tissue in between. The central core 220 of the button is thicker to retain strength. The button also features three holes (230, 240, and 250) that allow for the suture braid to be routed and rerouted to increase strength and prevent slippage of the suture.

Figure 3H:
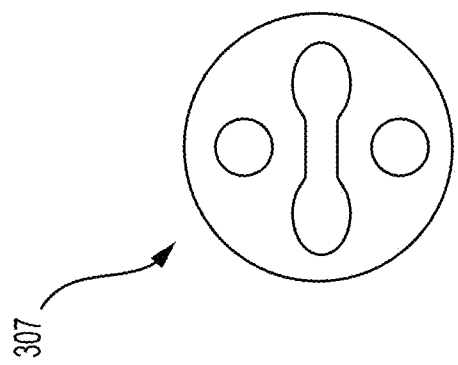
Figure 3G:
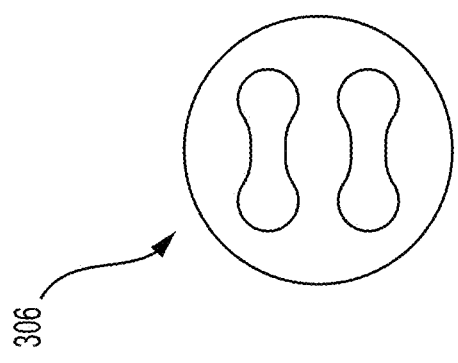
Figure 3F:
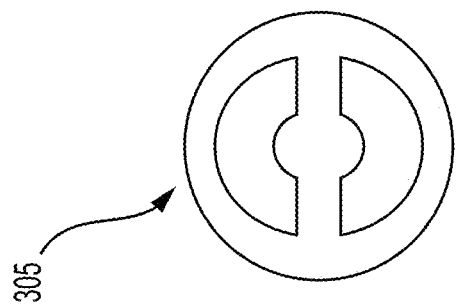

FIGS. 3A-3H depict alternative designs for the lateral button. FIG. 3A depicts a basic rounded lateral button 300 design with four apertures (310, 311, 312, 313) equally spaced in a circular pattern. FIG. 3B depicts a lateral button 301 designed to have a central core 320 thicker than the peripheral edge 330 with additional surface area to better distribute load across the bone surface. FIG. 3C depicts a lateral button 302 with a top hat 340 centrally situated on one side of the lateral button. This design is configured to improve interfacing with holes in various washers and plates. FIG. 3D depicts a lateral button 303 with an additional vertical aperture 350 centrally located on one side of the lateral button to provide additional area for suture passage. FIG. 3E depicts a lateral button 304 with a closed hook 360 situated on one side of the lateral button for self-locking. FIGS. 3F, 3G, and 3H depict other lateral buttons (305, 306, and 307, respectively).

Figure 4B:
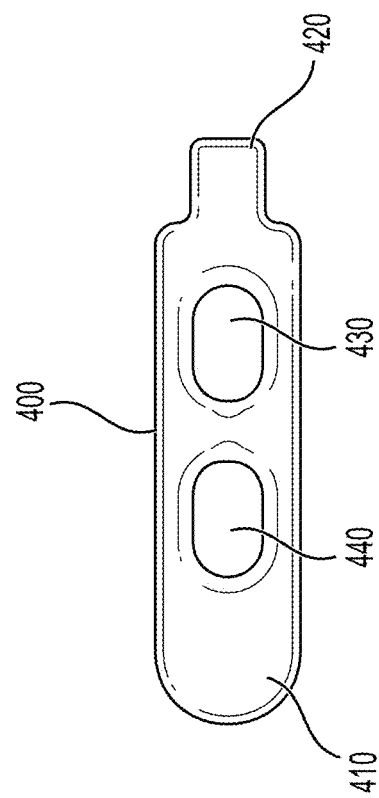
FIGS. 4A and 4B illustrate a schematic perspective view (FIG. 4A) and a top view (FIG. 4B) of an oblong medial button in accordance with the present disclosure.
Figure 4A:
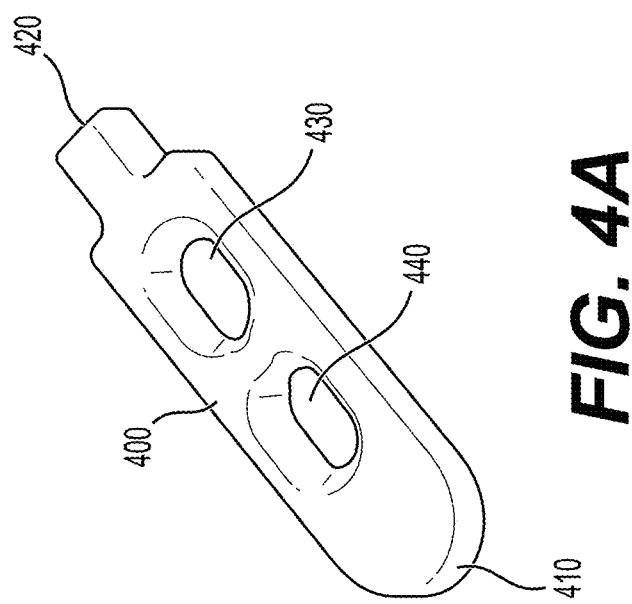

FIGS. 4A and 4B illustrate a schematic perspective view (FIG. 4A) and a top view (FIG. 4B) of an oblong medial button in accordance with the present disclosure. In one embodiment, the medial button 400 features a standard oblong shape to allow passage through the bone tunnel. Additionally, the medial button features rounded edges 410 at each corner of an oblong button to prevent soft tissue irritation. In another embodiment, the medial button 400 has a rectangular tab 420 at one end that allows the button to interface with the insertion rod of an inserter device and provides for controlled rotation and deployment on the medial side of the tibia. The medial button may have two apertures (430, 440) being located substantially about a longitudinal mid-line of the medial button that allow a flexible material, including suture strands, to pass or be threaded therethrough to form a flexible, adjustable, self-cinching suture connector of the disclosure.

Figure 5B:
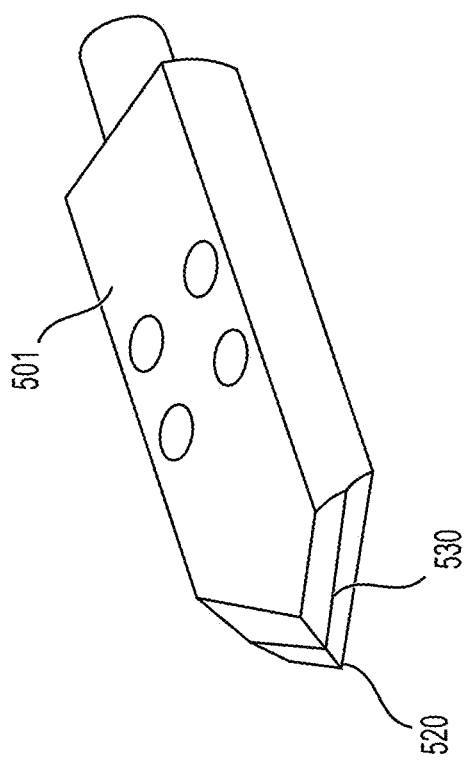
FIGS. 5A-5B illustrate alternative designs for the oblong medial button in accordance with the present disclosure.
Figure 5A:
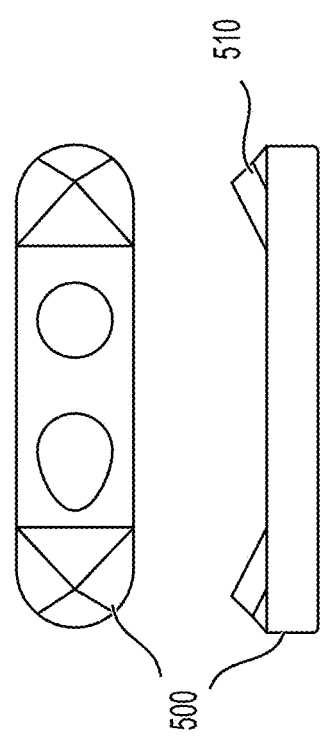

FIGS. 5A-5B depict alternative designs for the medial button. FIG. 5A depicts an oblong button 500 with ridges 510 on either side to provide additional traction when placed against the bone. FIG. 5B depicts an oblong button 501 with pointed faces 520 with bladed edges 530 to eliminate the need for pre-drilling as the bladed edge of the button can be used for self-drilling instead.

In one embodiment of the disclosure, a flexible connector comprises a plurality of suture strands looped through the medial button and the lateral button. In another embodiment, the suture strand is passed through at least one aperture in both the medial button and the lateral button. In another embodiment, the flexible connector comprises at least one free end extending through the lateral button. The flexible connector of the present disclosure allows the surgeon to apply and maintain tension by simply pulling a free end and without knot-tying.

Figure 6A:
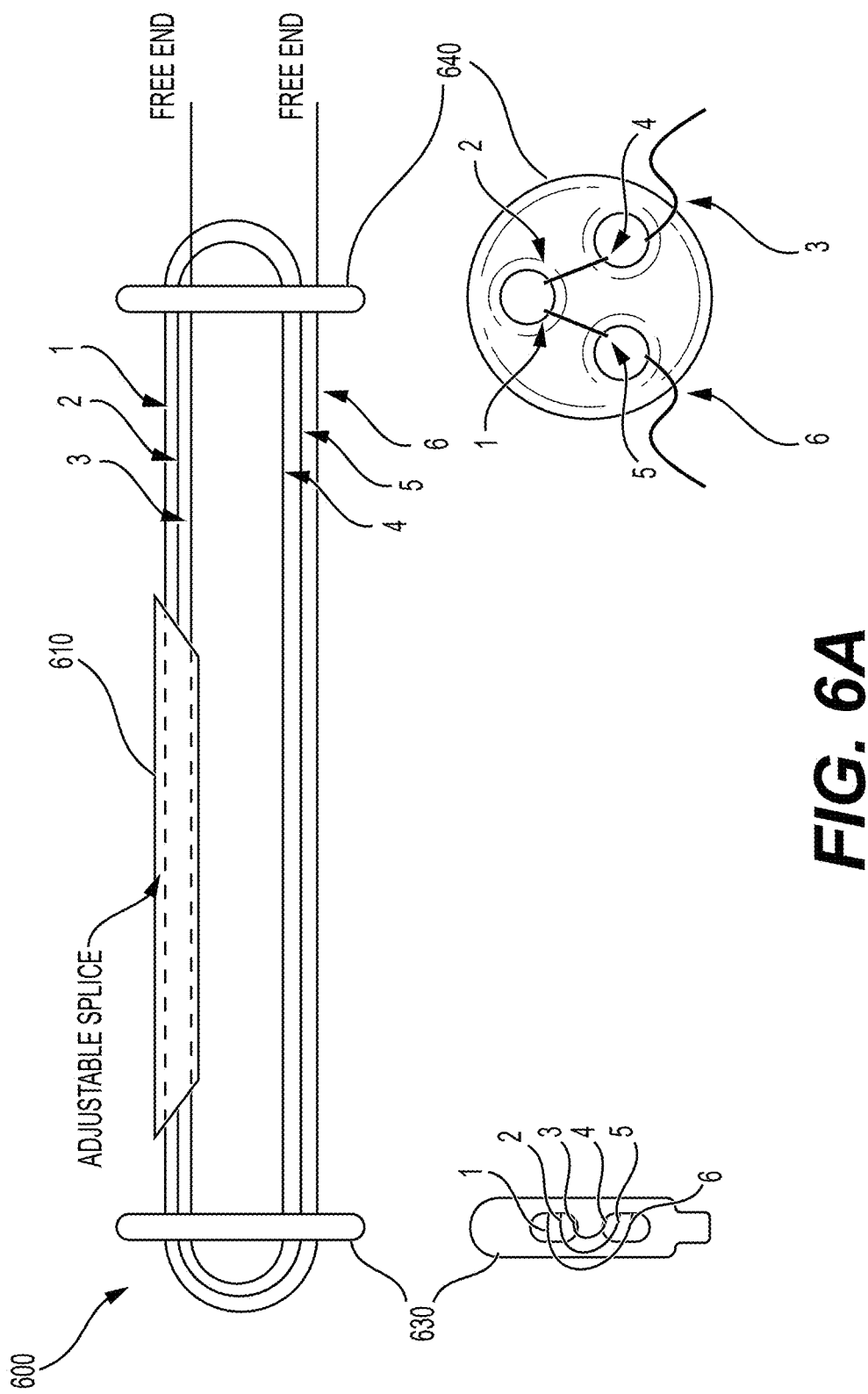
FIG. 6A illustrates an exemplary suture button assembly with splices in accordance with the present disclosure.
Figure 6B:
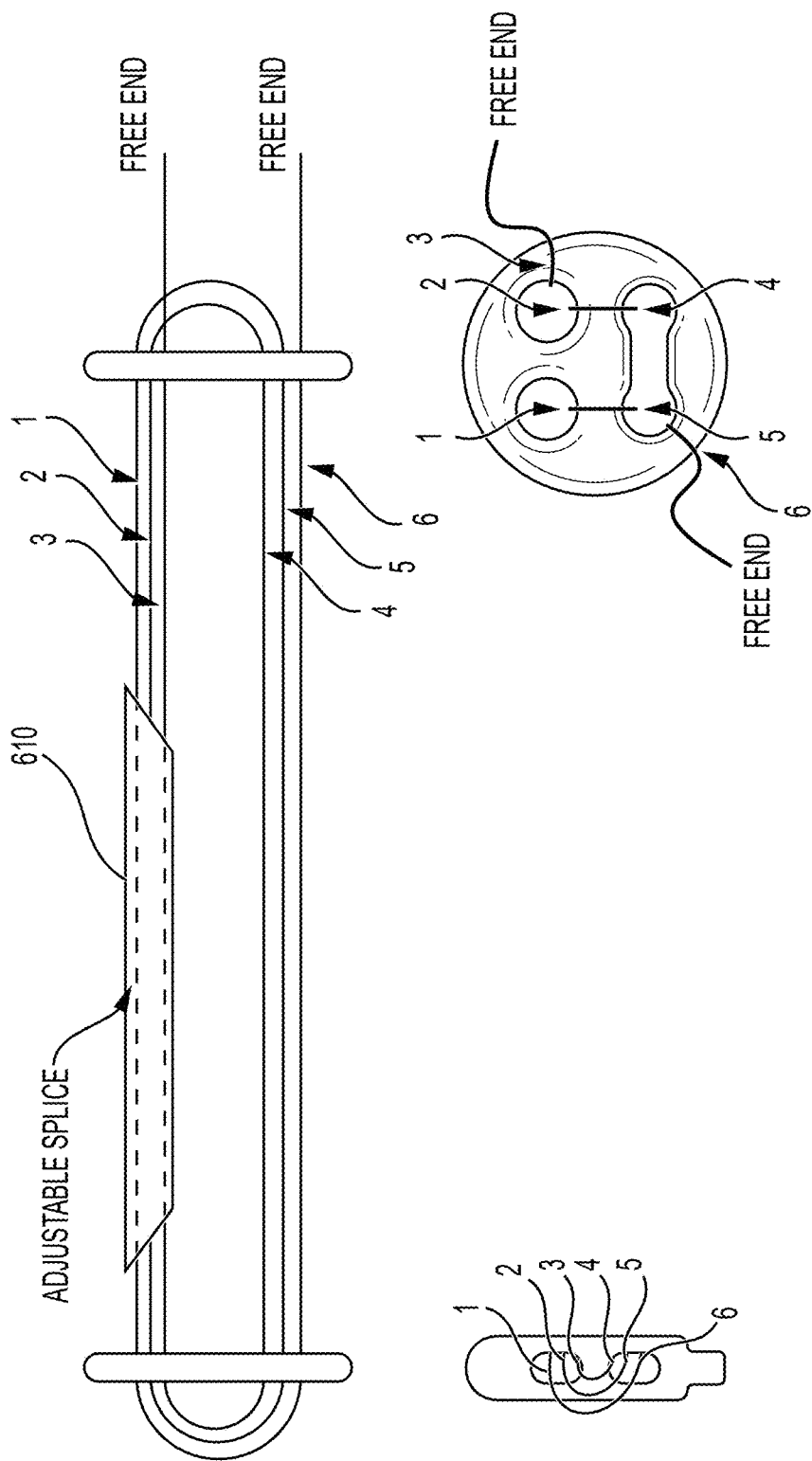
FIG. 6B illustrates an exemplary suture button assembly with splices in accordance with the present disclosure.

FIG. 6A depicts a flexible connector 600 with one exemplary suture assembly. According to the present disclosure, a flexible connector is composed of ultra-high molecular weight polyethylene (UHMWPE) assembled in a braided manner. The design features asymmetric knotless tensioning technology wherein one self-intersecting "splice" 610 is positioned between medial button 630 and lateral button 640. The splice is created by passing one section of a suture strand inside another section of the braided suture strand, so that the outer suture section essentially makes a tunnel for the section of suture that is passed through. After a certain distance, termed the "splice length", the inner suture exits the splice. More specifically, the leading and trailing edges of the suture braid are passed through the splice, as the braid is routed and rerouted between the medial and lateral buttons. As the free ends of the suture are tightened, the splice constricts against the inner sections of suture that were passed through, creating enough friction to allow for the knotless design. FIG. 6A depicts a symmetrical three hole button and FIG. 6B depicts an oblong 3 hole button design.

Figure 7B:
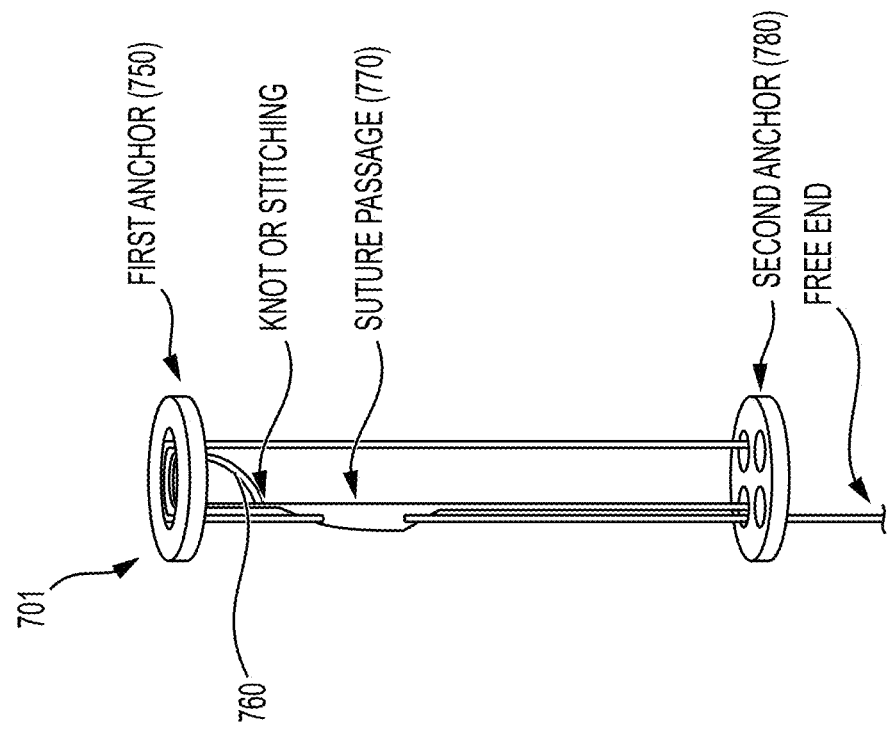
FIGS. 7A-7B depict alternative embodiments for the suture button braid assembly in accordance with the present disclosure.
Figure 7A:
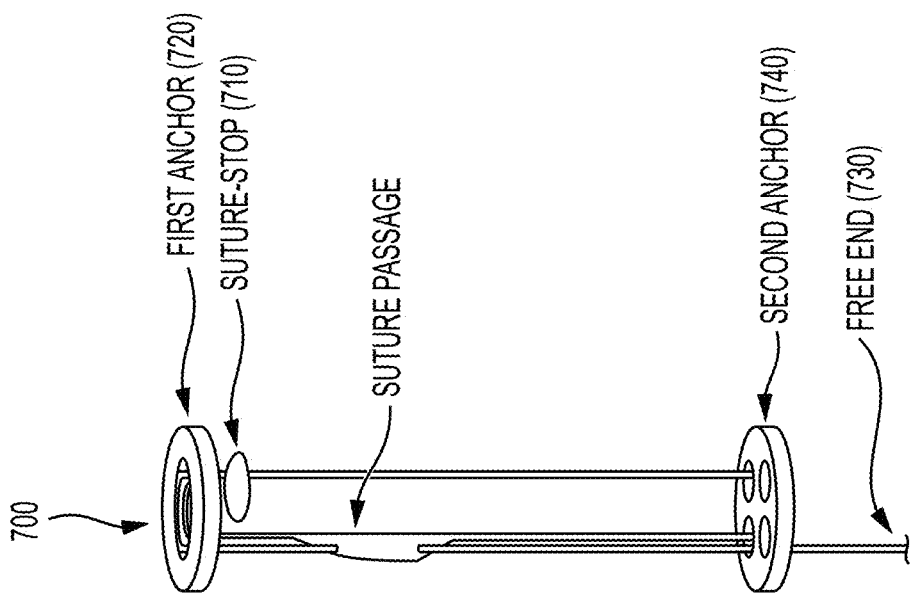

FIGS. 7A-7B depict alternative embodiments of the flexible connector. FIG. 7A illustrates a flexible connector 700 featuring knotted free end tensioning. One free end 710 of suture is secured to a first anchor 720 either by means of a hard-stop that prevents pull-through, including by tying a knot, or by attaching the free end to the anchor itself, or by other means of fixation. The opposite end 730 is looped through a second anchor 740 then back through the first anchor 720. FIG. 7B illustrates an embodiment of a flexible connector 701 featuring knotless free end tensioning. After exiting the first anchor 750 the free end 760 is passed through a suture passage 770. The suture passage is defined as a portion of the suture body that allows the suture to pass through itself. This can be accomplished by loose braiding in this portion only or simply by requiring loose braiding throughout the entire suture body. When the anchors are put in tension, the suture body containing the suture passage is put in tension and therefore constricts upon the suture passing through. This creates a self-cinching effect that prevents the assembly from backing out once assembled. After the free end is passed through the suture passage it is passed back through the second anchor (lateral button) 780.

FIG. 8 depicts one embodiment of a flexible connector 800 featuring a single splice suture braid assembly. This suture assembly is composed of ultra-high molecular weight polyethylene (UHMWPE) assembled in a braided manner. The design features a self-intersecting "splice" to allow for knotless tensioning. The splice 810 is created by passing one end of suture inside another section of the braided suture, so that the outer suture section essentially makes a tunnel for the section of suture that is passed through. After a certain distance, termed the "splice length", the inner suture exits the splice. More specifically, the leading and trailing edges of the suture braid are passed through the splice as the braid is routed and re-routed through the medial and lateral buttons. As the free ends of the suture are tightened, the splice constricts against the inner section of suture that was passed through, creating enough friction to allow for the knotless design.

Figures 10, 11:
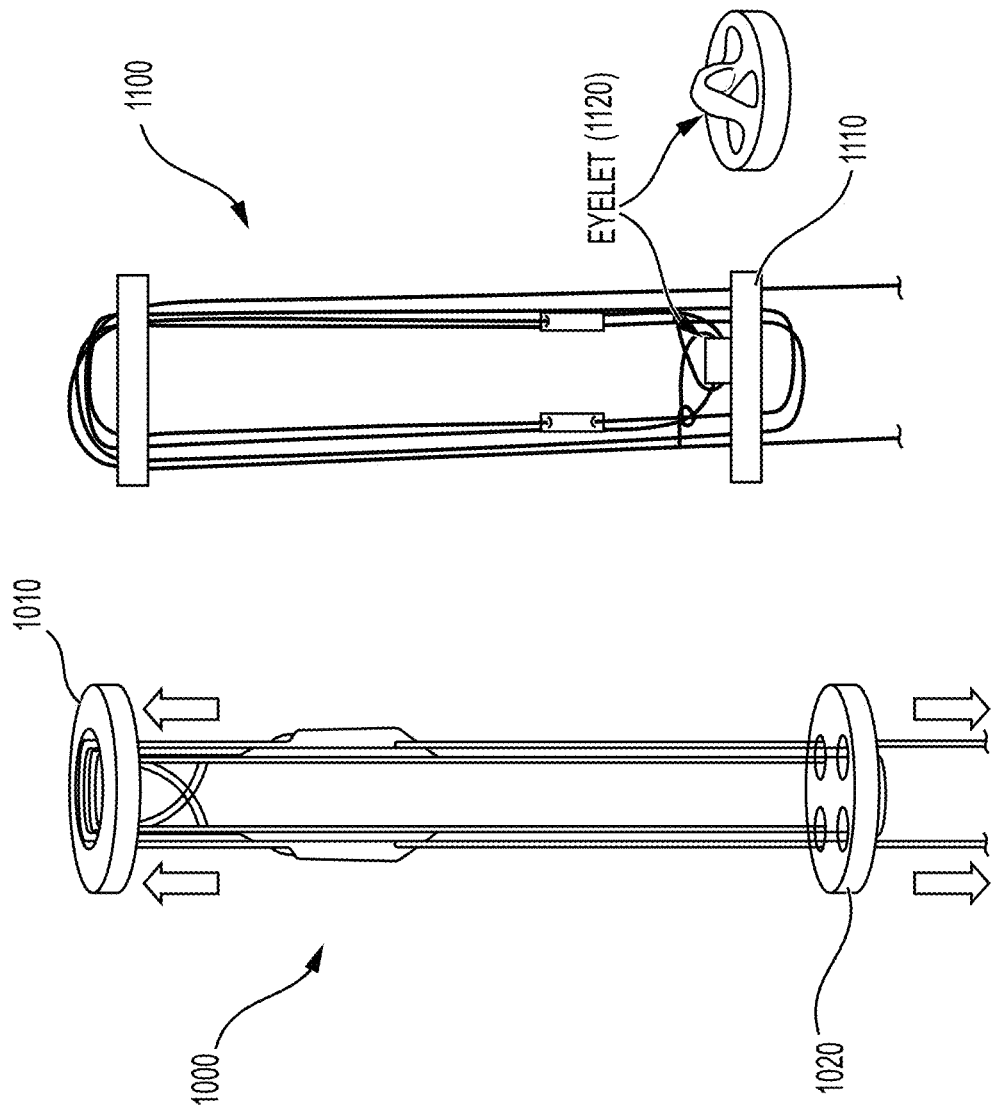
FIG. 10 depict one embodiment of a suture assembly in accordance with the present disclosure.
FIG. 11 depict one embodiment of a suture assembly in accordance with the present disclosure.

FIG. 9 depicts one embodiment of a flexible connector 900 featuring a single sided double splice braid assembly. This suture assembly is composed of ultra-high molecular weight polyethylene (UHMWPE) assembled in a braided manner. The design features knotless tensioning technology wherein two self-intersecting "splices" (910, 920) are positioned together on either side between the medial and lateral buttons. The trailing end of the suture braid is passed through the first splice and the leading end is routed from the second splice through the medial and then lateral button, while the braid is routed and rerouted between the medial and lateral buttons. As the free ends of the suture are tightened, the splices constrict against the inner section of suture that was passed through, creating enough friction to allow for the knotless design FIG. 10 depicts another embodiment of a flexible connector 1000. In this suture assembly, suture can be looped through the anchors (1010, 1020) in exactly the same manner in parallel to create a construct that has twice the tensile strength. The free ends of the suture strands may attach to an aperture in the round button.

FIG. 11 depicts another embodiment of a flexible connector 1100. In this suture assembly, an anchor 1110 with a vertical aperture 1120 centrally situated on one side is used. The suture can be looped through the vertical aperture along with the horizontal apertures spaced in a circular pattern within anchors in exactly the same manner in parallel to create a construct that has twice the tensile strength. The free ends of the suture passage may attach to an aperture in the round button.

When deploying the suture button implant across the bones, there are several methods and devices that surgeons will use.

K-wire placement utilizes incision sites on both the lateral and medial sides of the ankle. After drilling a bone tunnel through the lateral fibula, syndesmosis joint, and far medial tibia, a k-wire is passed through the bone tunnel and exits through the skin of the medial ankle. This k-wire has an aperture on the trailing end that pulls two suture lines. The shorter, taut suture line pulls the leading end of the oblong button through the bone tunnel. The longer, slack suture line is pulled once the oblong button has been pulled through to its position on the medial side of the tibia. Until the oblong button reaches its final position, tension is maintained on trailing suture lines connecting to the round button. This helps maintain lengthwise orientation of the oblong button through the bone tunnel. By pulling longer of the leading suture lines, the oblong button is flipped perpendicular to the bone tunnel, allowing it rest against the bone surface. The round button may then be tensioned down to the lateral bone surface so that the entire construct is able to hold reduction of the syndesmosis joint.

Combined button/drill bit placement places the suture button construct entirely from the lateral side of the ankle. This can be accomplished using an oblong button with self-drilling faces. The button is rotated in a drilling fashion at the end of an insertion rod with a detachable quick connect handle. The drilling button/rod can be advanced under power using the quick connect interface. Suture lines are protected during drilling by residing within the cannula of the insertion rod. Once the oblong drill/button has advanced through the medial tibia, the outer sleeve of the rod may be rotated to simultaneously unlatch the oblong button/drill bit and align a lengthwise groove in the insertion rod so that the suture lines exit into the bone tunnel as the rod is retracted. The oblong button can be manipulated through the skin to orient flat against bone in its final position.

Inserter placement utilizes a single incision site on the lateral side of the ankle. An inserter device is used to insert and position the flexible fixation implant. It is contemplated that an inserter device comprises a cannulated insertion rod fixedly attached to a handle that houses a structure for disengaging the medial button at the distal tip of the cannulated rod. After drilling a bone tunnel passing through the lateral fibula, syndesmosis joint, and far medial tibia, the insertion rod with attached medial button is inserted through the bone tunnel. The handle of the inserter has a feature which may disengage the medial button from the insertion rod and allow for placement on the medial side of the tibia. This obviates the need for a medial incision to place the medial button. The implant is then disengaged from the inserter and final tightening is performed either by hand or tensioning handles.

Figure 12:
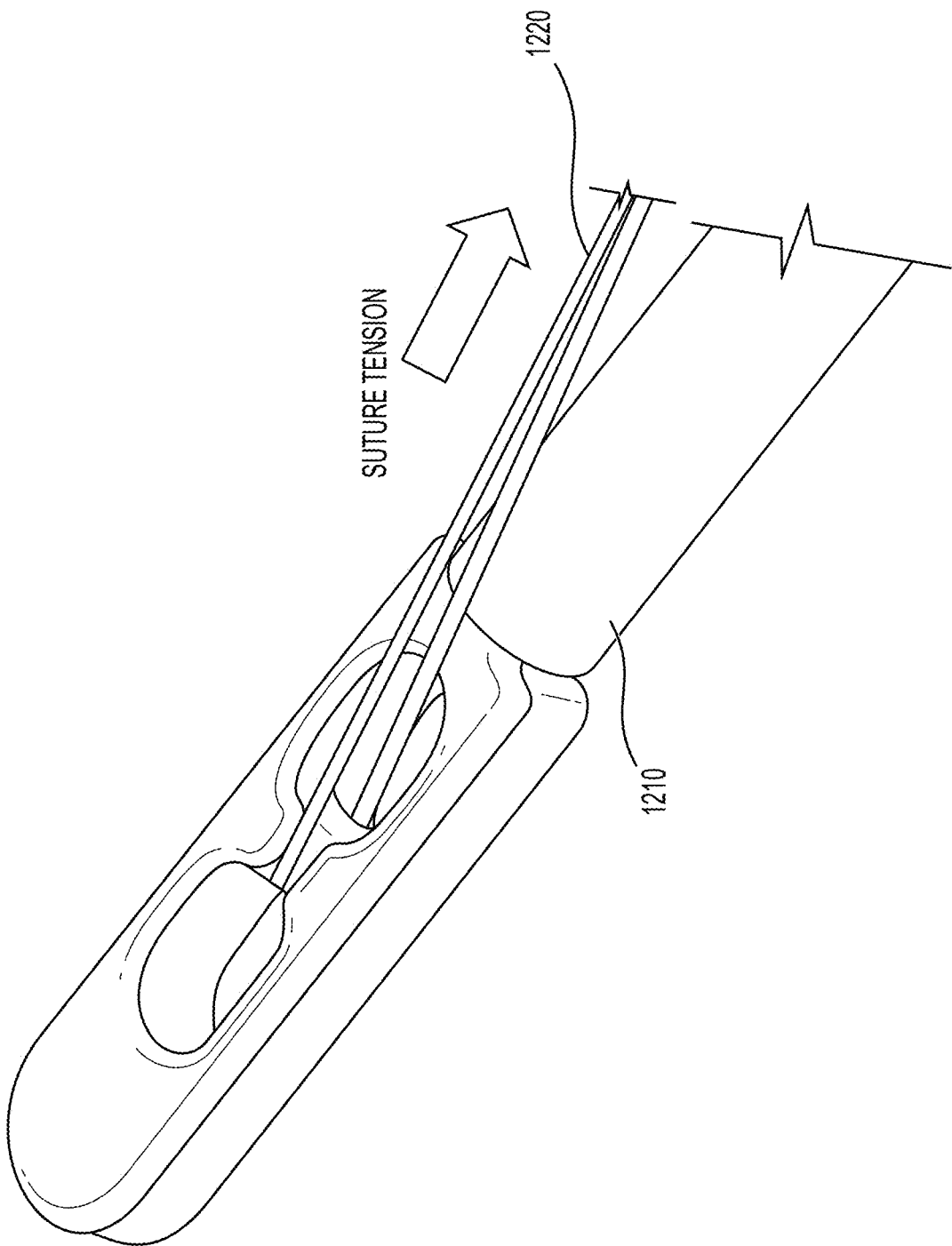
FIG. 12 illustrates a medial oblong button secured to a cannulated rod extending from the handle of the inserter device in accordance with the present disclosure.

As illustrated in FIG. 12, during placement, a rectangular tab at one end of the medial oblong button is attached to a cannulated rod 1210 extending from the handle of the inserter device. Suture strands 1220 route between the medial button and the lateral round button positioned on the handle. The tab of the medial button along with the tension in the suture lines keeps the button positioned on the cannulated rod and prevents it from falling off.

Figure 13A:
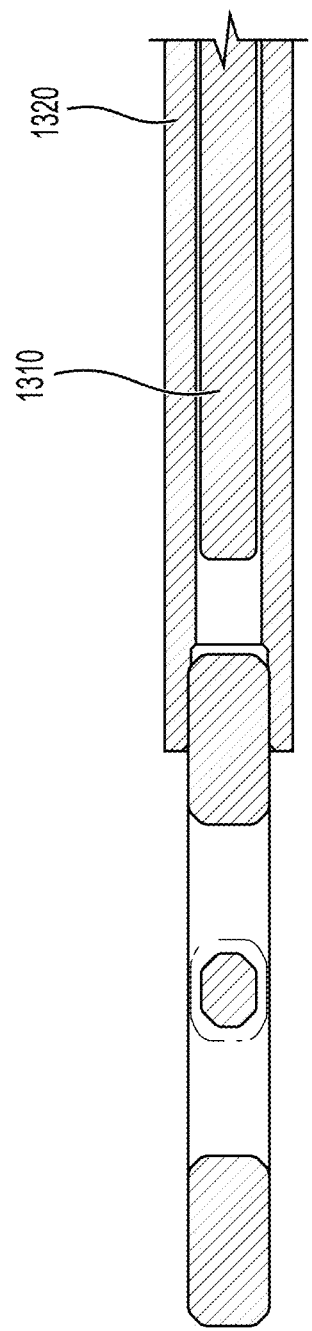
FIGS. 13A and 13B illustrate cross section views of the stationary inner rod extending through the outer cannulated rod of the handle.
Figure 13B:
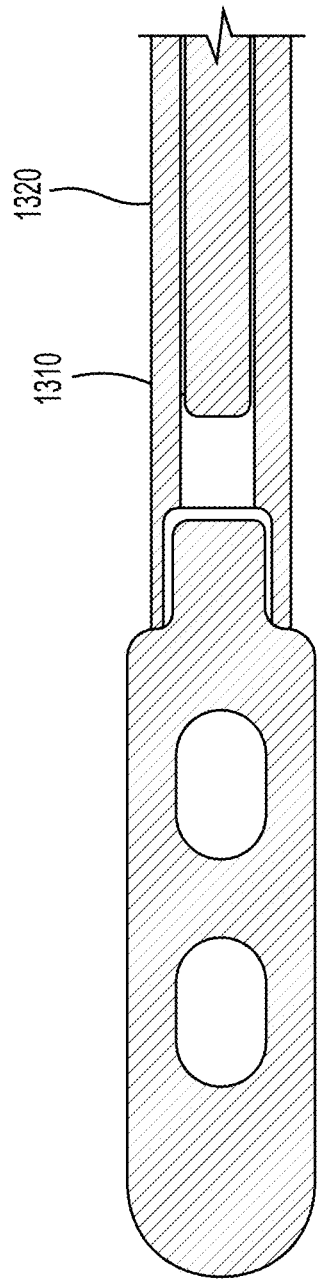

In some embodiments, as illustrated in FIG. 13, an inner rod 1310 extends through the outer cannulated rod 1320 of the handle. The inner rod 1310 is stationary and acts as a stopper so that the button is pushed off as the cannulated rod is retracted.

As depicted in FIG. 14A, tension in the suture lines 1410 keeps the oblong button flush against the outer cannulated rod 1420 and prevents it from falling off. A rectangular inlet 1430 (FIG. 14B) of the cannulated rod 1420 houses the tab of the medial oblong button 1440 and thus keeps the button rotationally constrained on the cannulated rod. Once the oblong button is at the desired position on the medial side of the bone tunnel, the oblong button is deployed by retracting the outer cannulated rod with activation at the handle. The cannulated rod and button both get retracted back until the button is pushed off by the inner stationary rod (FIG. 14C).

Figure 15A:
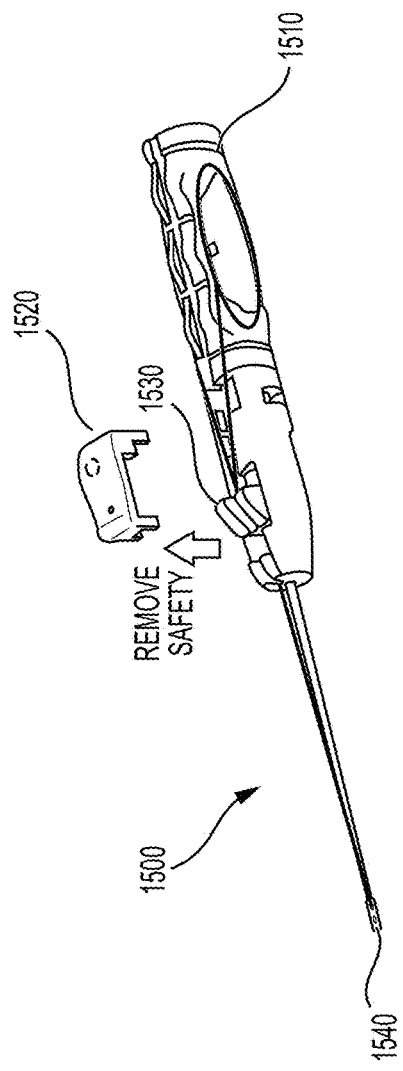
FIGS. 15A-15C illustrate steps of a method of decoupling an oblong button by retracting the cannulated rod away from the button using a pullback trigger on the inserter handle of the inserter device in accordance with the present disclosure.
Figure 15B:
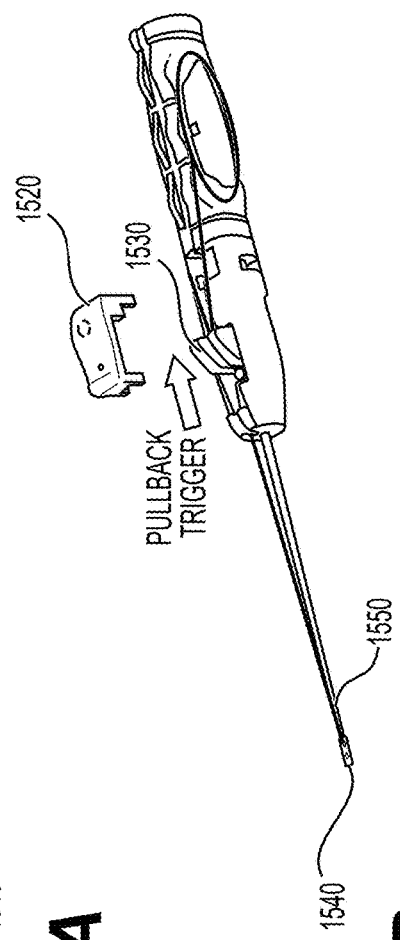
Figure 15C:
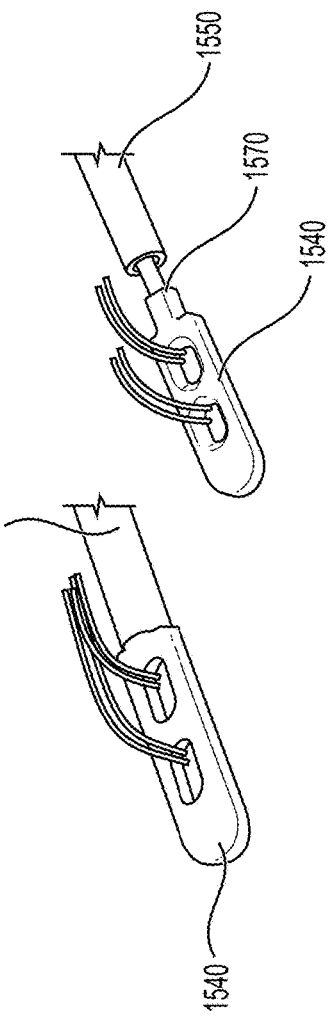

Referring to FIG. 15A, an inserter device 1500 may include a handle 1510 with a safety tap 1520 for preventing accidental button deployment. The safety tap may sit on top of a pullback trigger 1530 situated on the handle. Once the medial button 1540 is at the desired position on the medial side of the bone tunnel, the surgeon may remove a safety tab from the handle which safeguards accidental button deployment. Referring to FIG. 15B, once the safety tap 1520 has been removed, the button 1540 can be deployed by pulling a pullback trigger 1530 on the inserter handle to retract the cannulated rod 1550 away from the button 1540. Referring to FIG. 15C, as the cannulated rod 1550 retracts, a stationary inner rod which extends through the cannulated rod 1560 acts as a stopper for the tab 1570 of the button 1540. Once the cannulated rod 1550 retracts past the tip of the inner rod 1560, the button 1540 is pushed off the cannulated rod 1550 and deployed. The free medial button 1540 lies flat against the tibia bone on the medial side of the bone tunnel, and the round button is free to tension from the lateral side using a knotless tensioning mechanism.

Figure 16A:
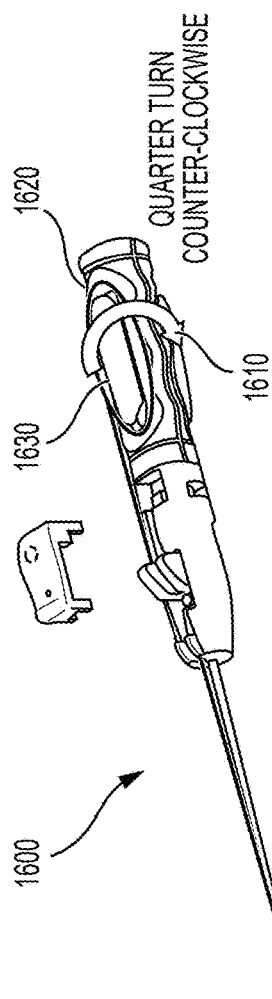
FIGS. 16A-16C illustrate steps of a method of tensioning a lateral button by an integrated tensioning handles in accordance with the present disclosure.
Figure 16B:
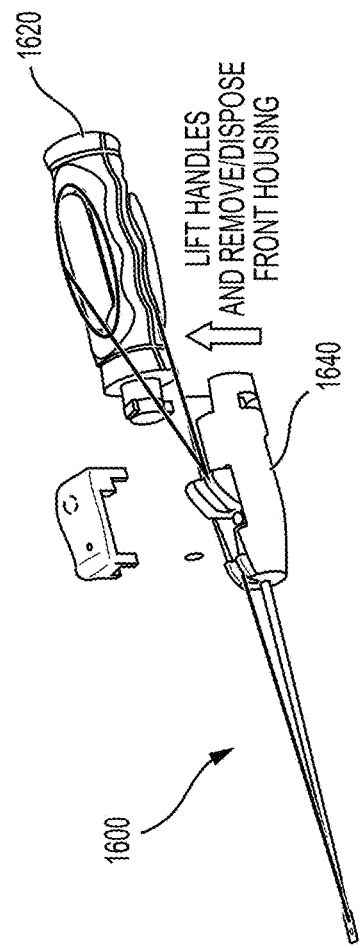
Figure 16C:
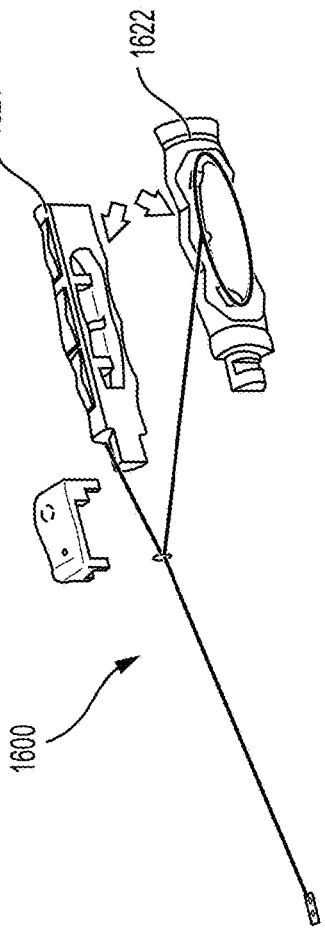

Referring to FIGS. 16A-16C, an inserter device 1600 may include a tensioning handle 1610 which is used to tension the lateral button. The tensioning handle 1610 comprises a detachable proximal portion 1620 with two anchor points 1630 and a distal housing 1640 for housing the lateral button. The two anchor point 1630 are located at the opposite lateral side of the proximal portion of the handle. Once the medial button has been deployed, a surgeon may deploy the tensioning handle by turning the proximal portion of the handle a counterclockwise quarter turn (FIG. 16A) and then lifting the proximal portion 1620 out of the distal housing 1640 (FIG. 16B). The proximal portion 1620 of the handle can then be separated into two halves (1621, 1622) and held in each hand to provide tensioning of the lateral button (FIG. 16C). The proximal portion of the handle features anchor points for excess suture line to be wrapped around and fixed in place with an O-ring. The configuration of the integrated tensioning handle of the present disclosure is highly advantageous in that (1) the handle helps prevent injury to the fingers and hands of surgeons, as lacerations can occur when tightening the suture by hand; (2) a surgeon is more likely to use integrated tensioning handles rather than make do without, reducing occurrence of injury; (3) procedure time is reduced since the surgeon will not need to request separate instruments for tensioning, and then spend time wrapping or clamping on the suture; and (4) there are fewer components to unpack or keep track of, reducing opportunity for dropping one in transfer or wasting time finding. This also simplifies packaging.

Figure 17A:
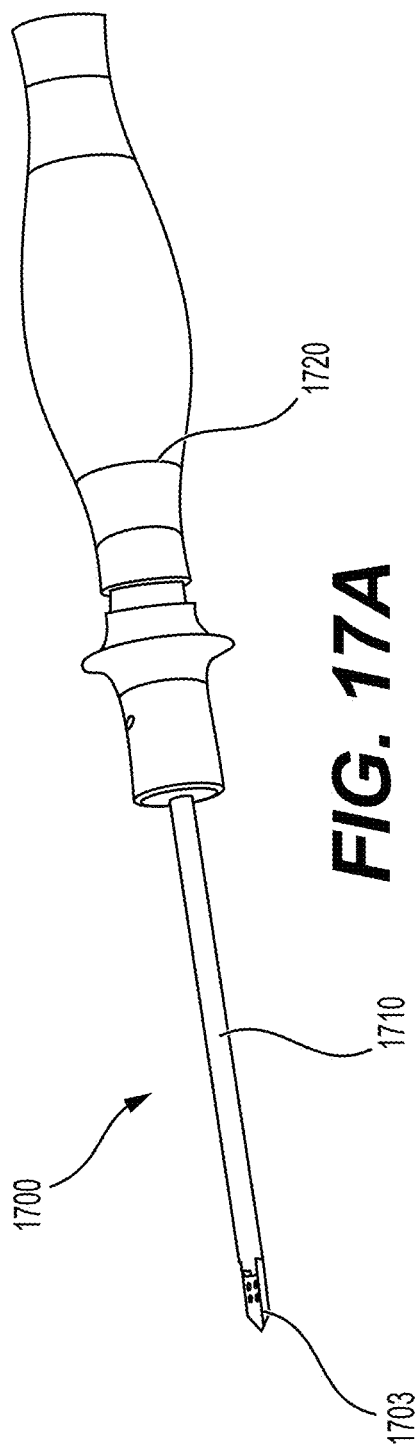
FIG. 17A depicts an embodiment of a self-drilling inserter in accordance with the present disclosure.
Figure 17B:
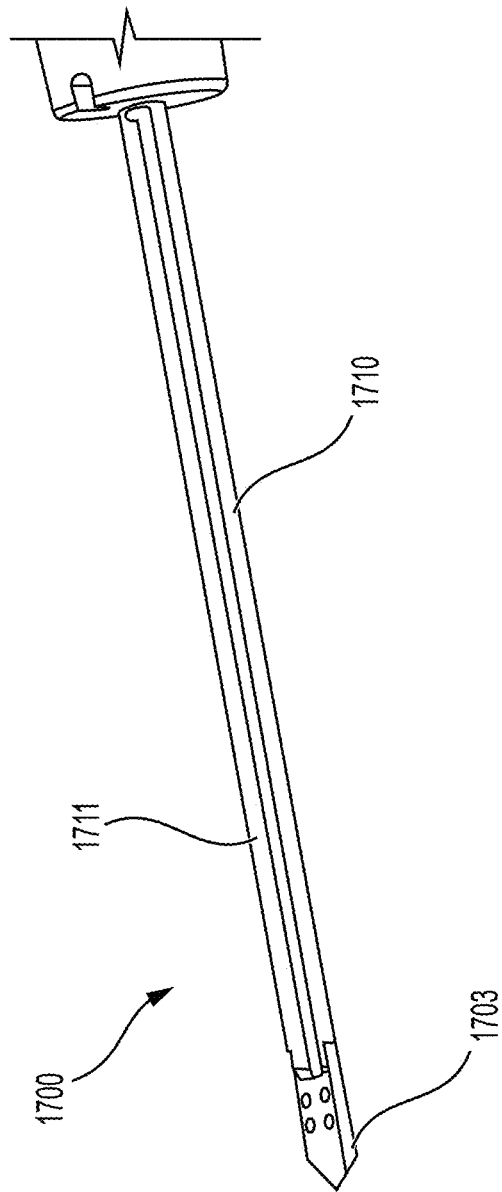
FIG. 17B depicts an embodiment of a self-drilling inserter in accordance with the present disclosure.

FIGS. 17A-17B depict an embodiment of a self-drilling inserter. The self-drilling inserter 1700 is to be used in conjunction with a self-drilling medial button as described in FIG. 5B. The button is rotated in a drilling fashion at the distal end of an insertion rod 1710 with a detachable quick connect handle 1720 (FIG. 17A). The drilling button 1730/rod 1710 can be advanced under power using the quick connect interface. Suture lines are protected during drilling by residing within the cannula of the insertion rod. Once the oblong self-drilling button 1730 has advanced through the medial tibia, the outer sleeve 1711 of the rod 1710 may be rotated to simultaneously unlatch the oblong button and align a lengthwise groove in the insertion rod so that the suture lines exit into the bone tunnel as the rod is retracted (FIG. 17B). The oblong button can be manipulated through the skin to orient flat against bone in its final position.

It is intended that all matter contained in the above description or shown in the accompanying drawings shall be interpreted as illustrative only and not limiting. Changes in detail or structure may be made without departing from the spirit of the disclosure as defined in the appended claims.

The invention claimed is:

1. A suture button system for fixing a syndesmotic injury, comprising:
   a flexible fixation implant; and
   an inserter device for positioning the flexible fixation implant across bones, the inserter device including:
      a distal housing defining a longitudinal axis;
      a first handle;
      a second handle removably attached to the first handle; and
      wherein the first and second handles are laterally disposed from each other and are removably attached to a proximal end of the distal housing;
   wherein the flexible fixation implant comprises a first suture button configured for passage through a bone tunnel in a first position and for positioning in a second position relative to a first bone; a second suture button configured for positioning relative to a second bone; and a flexible suture connector connected to the first suture button and the second suture button; wherein the flexible suture connector comprises a braided suture strand and first and second free ends, the first free end being pre-attached to the first handle and the second free end being pre-attached to the second handle;
   wherein the flexible suture connector is received through an aperture of the second suture button, and wherein the first and second free ends are tensionable by pulling the first and second handles away from each other to shorten a length of the flexible suture connector between the first suture button and the second suture button; and
   wherein the inserter device is configured for inserting the first suture button through the bone tunnel.

2. The system of claim 1, wherein the first suture button comprises an oblong configuration with two apertures and rounded edges.

3. The system of claim 2, wherein the first suture button comprises ridges on either side of the first suture button.

4. The system of claim 2, wherein the first suture button further comprises a tab at one end of the first suture button configured for interfacing with the inserter device during the passage through the bone tunnel.

5. The system of claim 4, wherein the first suture button further comprises a pointed self-drilling face at an end of the first suture button opposite to the tab.

6. The system of claim 1, wherein the second suture button comprises a circular configuration and the aperture of the second suture button includes three apertures.

7. The system of claim 6, wherein the second suture button further comprises a beveled peripheral edge.

8. The system of claim 6, wherein the second suture button further comprises a central core thicker than a peripheral edge.

9. The system of claim 6, wherein the second suture button further comprises a top hat centrally situated on one side of the second suture button.

10. The system of claim 6, wherein the second suture button further comprises a vertical aperture centrally located on one side of the second suture button.

11. The system of claim 1, wherein the flexible suture connector comprises a self-intersecting loop assembly positioned between the first suture button and the second suture button, wherein the self-intersecting loop assembly is formed by passing one section of the braided suture strand through another section of the braided suture strand and the self-intersecting loop assembly constricts against the section of the braided suture strand that is passed through when the first and second free ends of the flexible suture connector are tightened.

12. The system of claim 1, wherein one free end of the first and second free ends of the flexible suture connector is secured to the first suture button by means comprising a hard-stop, tying a knot, and attaching the free end to the first suture button that prevents pull-through and an opposite end of the first and second free ends of the flexible suture connector is looped through the second suture button and back through the first suture button.

13. The system of claim 1, wherein the flexible suture connector comprises a suture passage formed by loosening braiding in a portion of the braided suture strand and splicing another portion of the braided suture strand through the loosened portion of the braided suture strand.

14. The system of claim 1, wherein the first and second handles are configured to be detached from the distal housing by rotating the first and second handles relative to the distal housing.

* * * * *